United States Patent [19]

Edmonson et al.

[11] 4,398,034

[45] Aug. 9, 1983

[54] PROCESS FOR THE PREPARATION OF LOW MOLECULAR WEIGHT POLYESTERS FROM HYDROXYPIVALDEHYDE

[75] Inventors: William L. Edmonson; Anthony W. McCollum, both of Longview, Tex.

[73] Assignee: Eastman Kodak Company, Rochester, N.Y.

[21] Appl. No.: 315,795

[22] Filed: Oct. 28, 1981

[51] Int. Cl.³ .................... C07C 67/08; C07C 67/03
[52] U.S. Cl. ........................... 560/1; 528/272; 528/307; 528/308; 528/230; 528/234; 528/239; 528/237; 560/76; 560/84; 560/89; 560/91; 560/96; 560/98; 560/99; 560/190; 560/199; 560/204
[58] Field of Search .................. 560/1, 76, 89, 91, 96, 560/98, 99, 190, 199, 204, 84

[56] References Cited

U.S. PATENT DOCUMENTS 3,332,983  7/1967  Barie et al. ..................... 560/190
3,852,335 12/1974  Merger et al. .................. 560/189

FOREIGN PATENT DOCUMENTS 1246346  9/1971  United Kingdom .

*Primary Examiner*—Natalie Trousof
*Assistant Examiner*—Vera C. Clarke

*Attorney, Agent, or Firm*—David E. Cotey; Daniel B. Reece, III

[57] ABSTRACT

The present invention provides a process for the preparation of low molecular weight polyesters directly from hydroxypivaldehyde. The process comprises reacting dry hydroxypivaldehyde with a diester, a multifunctional ester, a diacid, a polyester, or a mixture thereof at a temperature of about 100° C. to 230° C. in the presence of a transesterification catalyst. Optionally, modifying glycols, triols, or polyols may also be added. Suitable catalysts include tetraisopropyl titanate, dibutyltin oxide, lithium hydroxide, and lithium alkoxide, with tetraisopropyl titanate being especially preferred. The reaction is preferably accomplished in two stages by heating the reaction mixture to about 130° C. for about three hours and subsequently heating the reaction mixture to about 190°–230° C. until the reaction is essentially complete. In an especially preferred embodiment, the low molecular weight polyesters are produced by the reaction of hydroxypivaldehyde with a diester such as dimethyl adipate, dimethyl cyclohexane-1,4-dicarboxylate, and dimethyl terephthalate. The low molecular weight polyester product typically exhibits a molecular weight of about 400–2000 and a hydroxyl number of about 100–300.

25 Claims, No Drawings

PROCESS FOR THE PREPARATION OF LOW MOLECULAR WEIGHT POLYESTERS FROM HYDROXYPIVALDEHYDE

BACKGROUND OF THE INVENTION

The present invention relates to low molecular weight polyesters which are prepared directly from hydroxypivaldehyde as a reactant.

It is known that hydroxypivaldehyde can be used as an intermediate in the preparation of drugs and polyesters. See, for example, Japanese Pat. No. 74 40443, which discloses a method for the preparation of hydroxypivaldehyde. However, due to the relative instability of hydroxypivaldehyde, prior art processes for the preparation of polyesters from hydroxypivaldehyde commonly include additional steps by which hydroxypivaldehyde is converted to a more stable ester prior to formation of the desired polyester. For example, U.S. Pat. No. 3,852,335 discloses the preparation of 2,2-dimethyl-1,3-propanediol-hydroxypivalic monoester which may then be used as a starting material for the manufacture of polyesters. U.S. Pat. No. 3,862,215 contains a similar disclosure.

The present invention provides a process by which low molecular weight polyesters are prepared directly from hydroxypivaldehyde as a reactant. The present process obviates the need for chemical conversion of the hydroxypivaldehyde prior to formation of the polyester, thereby eliminating one or more process steps. Consequently, there is a resulting savings in time and cost.

The product formed by the process of the present invention can be used in any application requiring a polyester diol or polyol. High solids coatings (75 weight percent or greater solids) prepared from the composition produced by the process of the present invention exhibit excellent gloss, solvent resistance, impact resistance, stain resistance, and humidity resistance.

The use of hydroxypivaldehyde as a reactant in the preparation of low molecular weight polyesters allows the introduction of unique neopentyl repeating units into the polyester. Hydroxypivaldehyde is readily available as the product of the reaction of isobutyraldehyde with formaldehyde.

SUMMARY OF THE INVENTION

The present invention provides a process for the preparation of low molecular weight polyesters. The process comprises reacting dry hydroxypivaldehyde with a diester, a multifunctional ester, a diacid, a polyester, or a mixture thereof at a temperature of about 100° C. to 230° C. in the presence of a transesterification catalyst.

DETAILED DESCRIPTION OF THE INVENTION

The present invention provides a process for the production of low molecular weight polyesters. The polyester product is produced by the reaction of dry hydroxypivaldehyde with a diester, a multifunctional ester, a diacid, a polyester, or a mixture thereof.

The hydroxypivaldehyde which is used in the process of the present invention is commonly obtained by the reaction of isobutyraldehyde with formaldehyde. In order to avoid deactivation of the catalyst, the hydroxypivaldehyde which is used in the process of the present invention is essentially free of water. Because hydroxypivaldehyde is usually prepared in aqueous solution, the hydroxypivaldehyde must be dried prior to reaction. The hydroxypivaldehyde may either be dried and then charged to the reaction system or it may be charged as an aqueous solution and the water subsequently driven from the system prior to addition of the catalyst. Whether dried before or after introduction to the reaction system, the hydroxypivaldehyde is commonly freed from water by distillation at appropriate combinations of temperature and pressure. Typical conditions may be, for example, a temperature of 75° C. and a pressure of 30 mm. The dry hydroxypivaldehyde is understood to exist as a complex mixture of hemiacetals and cyclic complexes.

Because of the tendency towards decarbonylation of the sensitive hydroxypivaldehyde molecule, it is also desirable to avoid the presence in the reaction system of strong acid. The presence of strong acid in the system tends to catalyze the decarbonylation reaction.

The diesters with which the dry hydroxypivaldehyde may be reacted include lower alkyl diesters of dicarboxylic acids. The lower alkyl groups contain 1-6 carbon atoms. Preferred lower alkyl groups are methyl groups. Dicarboxylic acids from which the lower alkyl diesters can be formed include adipic acid, cyclohexane-1,4-dicarboxylic acid, terephthalic acid, and other common dicarboxylic acids. Specific examples of suitable diesters include dimethyl adipate, dimethyl cyclohexane-1,4-dicarboxylate, and dimethyl terephthalate.

The polyesters with which the dry hydroxypivaldehyde may be reacted according to the process of the present invention include such common polyesters as polyethylene terephthalate, polybutylene terephthalate, polycyclohexanedimethanol terephthalate, the corresponding orthophthalates, the corresponding isophthalates, and other similar polyesters. The polyesters which are employed may have a molecular weight of about 1000 up to that represented by an inherent viscosity of about 2.0. These relatively high molecular weight polyesters are broken down during reaction with the dry hydroxypivaldehyde according to the process of the present invention to form the low molecular weight polyester product defined hereinafter.

Although not preferred as reactants in the process of the present invention, diacids may also be reacted with hydroxypivaldehyde to form the low molecular weight polyester product. The diacids are less preferred as reactants because their presence may lead to some decomposition of the hydroxypivaldehyde. However, the use of diacids is not thereby totally precluded. Specific examples of suitable diacids include isophthalic acid, adipic acid, terephthalic acid, orthophthalic acid, orthophthalic anhydride, etc.

In addition, modifying glycols, triols, or polyols may be included as reactants in the process of the present invention. Examples of such reactants include neopentyl glycol, dimethylpentanediol, propylene glycol, ethylene glycol, cyclohexanedimethanol, trimethylolpropane, pentaerythritol, dimethylolpropionic acid, and other well-known polyfunctional alcohols. The polyols may be added in order to impart some desired property such as higher hydroxyl number, higher molecular weight, etc.

In preferred embodiments, the dry hydroxypivaldehyde is reacted with one or more of the diesters described above. The molar ratio of dry hydroxypivaldehyde:diester commonly is about 2:1 to 8:1. Adjustments to the hydroxypivaldehyde:diester ratio affect the molecular weight of the resulting product. Thus, the molar ratio can be adjusted in order to achieve desired molecular weights. Such adjustments will be apparent to one of ordinary skill in the art, with increases in molecular weight being achieved by reductions in the amount of hydroxypivaldehyde utilized and, conversely, decreases in the molecular weight being achieved by increases in the hydroxypivaldehyde:diester ratio.

When dry hydroxypivaldehyde is reacted according to the process of the present invention with a polyester as described above, the hydroxypivaldehyde is present in the reaction mixture in an amount of about 10-60% by weight, based upon the total weight of reactants. Preferably, the hydroxypivaldehyde is present in an amount of about 40% by weight. Again, the amount of hydroxypivaldehyde present in the mixture influences the molecular weight of the product. Low concentrations of hydroxypivaldehyde yield a relatively high molecular weight product, whereas higher concentrations of hydroxypivaldehyde yield lower molecular weights. Thus, the relative amount of hydroxypivaldehyde utilized will depend upon the molecular weight of the reactant polyester and upon the desired molecular weight of the product polyester. The selection of an appropriate hydroxypivaldehyde concentration for the desired molecular weight product will be apparent to one of ordinary skill in the art.

The process of the present invention comprises reacting dry hydroxypivaldehyde with one or more of the other reactants described above at a temperature of about 100° C.-230° C. in the presence of a transesterification catalyst. Specific catalysts which may be employed in the process of the present invention include tetraisopropyl titanate, dibutyltin oxide, lithium hydroxide, and lithium alkoxide. The preferred catalyst is tetraisopropyl titanate. The catalyst is employed in an amount of about 0.01-1.0% by weight, based upon the weight of dry hydroxypivaldehyde. Preferably, the catalyst is present in an amount of about 0.1% by weight.

While the desired reaction occurs within the range indicated above, it is preferable to operate at temperatures within the range of approximately 190°-230° C. in order to complete the reaction within a reasonable time period and in order to drive the reaction to completion. However, in order to minimize decomposition of the hydroxypivaldehyde, it is desirable to conduct a prereaction at temperatures within the range of approximately 100°-130° C. Thus, in preferred embodiments, the reaction is conducted at a temperature within the range of approximately 100°-130° C. for about three hours, and the temperature is subsequently raised to about 190°-230° C., at which temperature the reaction is conducted until the reaction is essentially complete (e.g., about two hours).

The resulting low molecular weight polyester exhibits a molecular weight of about 400-2000 when measured by a boiling point elevation procedure. Preferably, the molecular weight of the product is within the range of about 400-800. The product typically exhibits a hydroxyl number of about 100-300.

The low molecular weight polyester produced by the process of the present invention contains at least three repeating units. Formula I illustrates the structure obtained when hydroxypivaldehyde is reacted with a diester having the formula CH₃OOCRCOOCH₃, where R is aliphatic or aromatic.

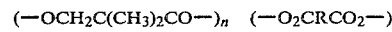

The units arising from hydroxypivaldehyde are units (1) and (2). The unit derived from the diester component is shown as (3). Thus, according to the present invention, hydroxypivaldehyde is converted in the presence of a suitable catalyst to neopentyl glycol substructure (1) and polyhydroxypivalic acid substructure (2), where n=1-5 depending upon the relative weight ratios of reactants and the reaction conditions.

The low molecular weight polyester product which contains the unique neopentyl repeating unit can be used in any application requiring a polyester diol or polyol. High solids coatings (75 weight % or greater solids) prepared from the product of the process of the present invention exhibit excellent gloss, solvent resistance, impact resistance, stain resistance, and humidity resistance.

The present invention provides a means for obtaining the low molecular weight polyester products directly from hydroxypivaldehyde as a reactant. The process of the present invention thereby eliminates one or more steps commonly encountered in prior art processes for the formation of polyesters from hydroxypivaldehyde by overcoming the need for separate steps for disproportionation of the hydroxypivaldehyde and/or the formation of more stable intermediates.

The invention will be further illustrated by the following Examples although it will be understood that these Examples are included merely for purposes of illustration and are not intended to limit the scope of the invention.

EXAMPLE 1

This Example illustrates the reaction of hydroxypivaldehyde with dimethyl terephthalate.

A reaction vessel was charged with 68 parts of dry hydroxypivaldehyde and 32 parts of dimethyl terephthalate. The reaction vessel was heated to 90°-100° C. 0.1% by weight, based upon the weight of dry hydroxypivaldehyde, of tetraisopropyl titanate was then added, and the temperature was increased to 130° C. After three hours at 130° C., the temperature was increased to 190° C., and the reaction was continued until methanol liberation ceased. The polyester resin so produced exhibited the following properties:

| | |
|---|---|
| Acid Number | <1 |
| Hydroxyl Number | 200 |
| Molecular Weight (by boiling point elevation) | 572 |
| Viscosity (at 100° F.) | 34500 cp |

A coating formulation was prepared by charging a ball mill with 202 grams of the polyester resin prepared as described above, 21 grams of xylene, 53 grams of Cymel 303 (registered trademark of American Cyanamid for hexamethoxymethyl melamine crosslinking resin), 169 grams of titanium dioxide pigment (Du Pont R-900), and 35 grams of a solvent blend composed of methyl ethyl ketone/an acetate of Ektasolve EE (registered trademark of Eastman Kodak for ethylene glycol monoethyl ether solvent)/n-butanol (50/30/20). The mixture was ground until a Hegman grind of 7-8 was achieved, and then 3.2 grams of Cycat 4040 (trademark of American Cyanamid for p-toluenesulfonic acid catalyst solution) and 13 grams of additional solvent blend were introduced. After mixing, the enamel so produced was spray applied to 20 gauge steel panels treated with phosphoric acid (Bonderite 1000). The coated panels were cured by baking for 20 minutes at 300° F. The resulting coating exhibited excellent gloss, solvent resistance, flexibility, and humidity resistance. The coatings further exhibited an impact resistance of 150/85 (F/R) inch-pound.

EXAMPLE 2

This Example illustrates the reaction of hydroxypivaldehyde with polyethylene terephthalate.

A reaction vessel was charged with 44 parts of dry hydroxypivaldehyde and 56 parts of polyethylene terephthalate. The reaction vessel was then heated to 100° C. 0.1% by weight, based upon the weight of the reactants, of tetraisopropyl titanate was added, and the temperature of the reaction vessel was increased to 130° C. After three hours at 130° C., the temperature was increased to 230° C. and held there for two hours. Heating was then discontinued, and the polyester product was collected. The product exhibited the following properties.

| | |
|---|---|
| Acid Number | 2 |
| Hydroxyl Number | 225 |
| Molecular Weight (by boiling point elevation) | 525 |

A ball mill was charged with 200 grams of the polyester produced as described above, 22 grams of methyl amyl ketone, 60 grams of Cymel 303 crosslinking resin, 173 grams of titanium dioxide pigment (Du Pont R-900), and 40 grams of the solvent blend described in Example 1. The mixture was then ground until a Hegman grind of 7-8 was obtained, and then 3.2 grams of Cycat 4040 catalyst solution (p-toluenesulfonic acid) and 16 grams of additional solvent blend were added. The resulting enamel was spray applied to steel panels and cured as described in Example 1. The resulting coating exhibited excellent gloss, solvent resistance, and humidity resistance. The coating further exhibited an impact resistance of 75/25 (F/R) inch-pounds.

EXAMPLE 3

This Example illustrates the reaction of hydroxypivaldehyde with dimethyl terephthalate and trimethylolpropane.

A reaction vessel was charged with 49 parts of dry hydroxypivaldehyde, 13 parts of trimethylolpropane, and 38 parts of dimethyl terephthalate. The reaction vessel was heated to 100° C. 0.1% by weight, based upon the weight of hydroxypivaldehyde, of tetraisopropyl titanate was then added, and the temperature was increased to 130° C. After three hours at 130° C., the temperature was increased to 185°-200° C., and the reaction was continued until methanol liberation ceased. The polyester so produced exhibited a hydroxyl number of 240.

A ball mill was charged with 150 grams of the polyester prepared as described above, 47.8 grams of Cymel 303 crosslinking resin, 132 grams titanium dioxide pigment (Du Pont R-900), and 70 grams of a solvent blend of methyl amyl ketone/Ektasolve EE acetate/n-butanol (50/30/20). The mixture was then ground until a Hegman grind of 7-8 was obtained, and then 2.0 grams of a 10% solution of L-5310 (a silicone flow control additive available from 3M) in Ektasolve EE acetate, 2.5 grams of Cycat 4040 catalyst solution, and 9.4 grams of additional solvent blend were added. The resulting enamel was spray-applied to steel panels and cured as described in Example 1. The resulting coating exhibited excellent gloss, solvent resistance, humidity resistance, and pencil hardness.

The invention has been described in detail with particular reference to preferred embodiments thereof, but it will be understood that variations and modifications can be effected within the spirit and scope of the invention.

We claim:

1. A process for the preparation of low molecular weight polyesters which comprises reacting dry hydroxypivaldehyde with a diester, a diacid, a polyester, or a mixture thereof at a temperature of about 100° C. to about 230° C. in the presence of a transesterification catalyst.

2. The process of claim 1 wherein a polyol or a mixture of polyols is added as a reactant.

3. The process of claim 1 wherein said catalyst is selected from the group consisting of tetraisopropyl titanate, dibutyltin oxide, lithium hydroxide, and lithium alkoxide.

4. The process of claim 1 wherein said catalyst is tetraisopropyl titanate.

5. The process of claim 1 wherein said catalyst is employed in an amount of about 0.01 to 1.0% by weight, based upon the weight of dry hydroxypivaldehyde.

6. The process of claim 1 wherein said catalyst is employed in an amount of about 0.1% by weight, based upon the weight of dry hydroxypivaldehyde.

7. The process of claim 1 wherein said dry hydroxypivaldehyde is reacted with a diester.

8. The process of claim 1 wherein said diester is a lower alkyl diester of a dicarboxylic acid, the lower alkyl groups containing 1 to 6 carbon atoms.

9. The process of claim 1 wherein said diester is selected from the group consisting of dimethyl adipate, dimethyl cyclohexane-1,4-dicarboxylate, and dimethyl terephthalate.

10. The process of claim 7 wherein the molar ratio of dry hydroxypivaldehyde:diester is about 2:1 to 8:1.

11. The process of claim 1 wherein said dry hydroxypivaldehyde is reacted with a diacid.

12. The process of claim 1 wherein said diacid is selected from the group consisting of isophthalic acid, terephthalic acid, adipic acid, orthophthalic acid, orthophthalic anhydride, and mixtures thereof.

13. The process of claim 1 wherein said dry hydroxypivaldehyde is reacted with a polyester.

14. The process of claim 13 wherein said polyester reactant is selected from the group consisting of the polymeric products of the reaction of ethylene glycol, butylene glycol, cyclohexanedimethanol, or mixtures thereof with terephthalic acid, isophthalic acid, orthophthalic acid, or mixtures thereof.

15. The process of claim 1 wherein said dry hydroxypivaldehyde is present in an amount of about 10 to 60% by weight.

16. The process of claim 15 wherein said dry hydroxypivaldehyde is present in an amount of about 40% by weight.

17. A process for the preparation of low molecular weight polyesters which comprises reacting dry hydroxypivaldehyde with a lower alkyl diester of a dicarboxylic acid, the lower alkyl groups containing 1 to 6 carbon atoms, in a molar ratio of dry hydroxypivaldehyde:diester of about 2:1 to 8:1 at a temperature of about 100° to 230° C. in the presence of about 0.1% by weight, based upon the weight of dry hydroxypivaldehyde, of a transesterification catalyst selected from the group consisting of tetraisopropyl titanate, dibutyltin oxide, lithium hydroxide, and lithium alkoxide.

18. The process of claim 17 wherein said dry hydroxypivaldehyde is reacted with said lower alkyl diester at a temperature of about 100°–130° C. for about three hours and subsequently at a temperature of about 190°–230° C. until the reaction is essentially complete.

19. The process of claim 17 wherein a polyol or a mixture of polyols is added as a reactant.

20. The process of claim 17 wherein said catalyst is tetraisopropyl titanate.

21. The process of claim 17 wherein said diester is selected from the group consisting of dimethyl adipate, dimethyl cyclohexane-1,4-dicarboxylate, and dimethyl terephthalate.

22. A process for the preparation of low molecular weight polyesters which comprises reacting about 10 to 60 percent by weight based upon the total weight of the reaction of dry hydroxypivaldehyde with a polyester reactant selected from the group consisting of the polymeric products of the reaction of ethylene glycol, butylene glycol, cyclohexanedimethanol, or mixtures thereof with terephthalic acid, isophthalic acid, orthophthalic acid, or mixtures thereof, said dry hydroxypivaldehyde being reacted with said polyester reactant at a temperature of about 100° to 230° C. in the presence of about 0.1% by weight, based upon the weight of dry hydroxypivaldehyde, of a transesterification catalyst selected from the group consisting of tetraisopropyl titanate, dibutyltin oxide, lithium hydroxide, and lithium alkoxide.

23. The process of claim 22 wherein a polyol or a mixture of polyols is added as a reactant.

24. The process of claim 22 wherein said catalyst is tetraisopropyl titanate.

25. The process of claim 22 wherein said dry hydroxypivaldehyde is present in an amount of about 40% by weight, based upon the total weight of reactant.

* * * * *